United States Patent
Schulte et al.

(10) Patent No.: US 9,995,695 B2
(45) Date of Patent: Jun. 12, 2018

(54) RADIOGRAPHY AND COMPUTED TOMOGRAPHY WITH HIGH-ENERGY ELECTRON BEAMS

(71) Applicant: LOMA LINDA UNIVERSITY, Loma Linda, CA (US)

(72) Inventors: Reinhard W. Schulte, Loma Linda, CA (US); Vladimir A. Bashkirov, Loma Linda, CA (US)

(73) Assignee: Loma Linda University, Loma Linda, CA (US)

( * ) Notice: Subject to any disclaimer, the term of this patent is extended or adjusted under 35 U.S.C. 154(b) by 0 days. days.

(21) Appl. No.: 15/318,840

(22) PCT Filed: Jun. 15, 2015

(86) PCT No.: PCT/US2015/035866
§ 371 (c)(1),
(2) Date: Dec. 14, 2016

(87) PCT Pub. No.: WO2015/195570
PCT Pub. Date: Dec. 23, 2015

(65) Prior Publication Data
US 2017/0160211 A1 Jun. 8, 2017

Related U.S. Application Data

(60) Provisional application No. 62/012,854, filed on Jun. 16, 2014.

(51) Int. Cl.
*G01N 23/00* (2006.01)
*G01N 23/04* (2018.01)
(Continued)

(52) U.S. Cl.
CPC .......... *G01N 23/046* (2013.01); *A61B 6/032* (2013.01); *A61B 6/14* (2013.01); *A61B 6/4258* (2013.01);
(Continued)

(58) Field of Classification Search
None
See application file for complete search history.

(56) References Cited

U.S. PATENT DOCUMENTS 4,287,425 A * 9/1981 Elliott, Jr. .............. A61B 6/032
250/398
4,691,332 A * 9/1987 Burstein ................ G01N 23/04
378/11

(Continued)

OTHER PUBLICATIONS

S. Izumi et al.; "High Energy X-ray Computed Tomography for Industrial Applications"; IEEE Transactions on Nuclear Science, vol. 40, No. 2; Apr. 1993; pp. 158-161.
(Continued)

*Primary Examiner* — Andrew Smyth
(74) *Attorney, Agent, or Firm* — Potomac Law Group, PLLC

(57) ABSTRACT

An imaging system can use high-energy electrons at a low dose level to generate 3D computed tomography images and/or 2D radiographic images of living tissue and other objects. In some embodiments, a nozzle directs a source of high-energy electrons to the imaging target, and a detector system detects physical quantities of electrons that interact with the imaging target. In some embodiments, a computer system can calculate estimated paths taken by individual electrons within the imaging target, determine interactions between voxels of a digitized image of the imaging target and individual electrons, and reconstruct a digitized image of the imaging target based at least in part on the determined interactions between individual electrons and voxels. The (Continued)

imaging target can include but is not limited to living tissue, humans, pediatric patients, small animals, and other objects, such as those used in industrial applications.

20 Claims, 5 Drawing Sheets

(51) Int. Cl.
    *A61B 6/03*     (2006.01)
    *A61B 6/00*     (2006.01)
    *G06T 11/00*     (2006.01)
    *A61B 6/14*     (2006.01)
    *G06T 7/00*     (2017.01)

(52) U.S. Cl.
    CPC .............. *A61B 6/501* (2013.01); *A61B 6/502* (2013.01); *A61B 6/503* (2013.01); *A61B 6/5205* (2013.01); *G06T 7/0012* (2013.01); *G06T 11/003* (2013.01); *G06T 11/006* (2013.01); *G01N 2223/102* (2013.01); *G06T 2207/10028* (2013.01); *G06T 2207/10081* (2013.01); *G06T 2207/30016* (2013.01); *G06T 2207/30036* (2013.01); *G06T 2207/30048* (2013.01); *G06T 2207/30061* (2013.01); *G06T 2207/30068* (2013.01); *G06T 2207/30084* (2013.01)

(56) References Cited

U.S. PATENT DOCUMENTS

| 6,477,223 B1* | 11/2002 | Francke ................. A61B 6/032 378/146 |
| 6,628,745 B1* | 9/2003 | Annis .................... A61B 6/032 378/10 |
| 2007/0009081 A1 | 1/2007 | Zhou et al. |
| 2011/0220794 A1* | 9/2011 | Censor ................. G01N 23/046 250/307 |

OTHER PUBLICATIONS

F. Beekman et al.; "Efficient Fully 3-D Iterative SPECT Reconstructions With Monte Carlo-BAsed Scatter Compensation"; IEEE Transactions on Medical Imaging, vol. 21, No. 8; Aug. 2002; pp. 867-877.

Extended European Search Report dated Feb. 13, 2018 for related European Application No. 15809530.7.

* cited by examiner

RADIOGRAPHY AND COMPUTED TOMOGRAPHY WITH HIGH-ENERGY ELECTRON BEAMS

RELATED APPLICATION

This application claims the benefit under 35 U.S.C. § 119(e) of U.S. Provisional Application No. 62/012,854, filed Jun. 16, 2014, titled COMPUTED TOMOGRAPHY WITH HIGH-ENERGY ELECTRON BEAMS. The entire contents of the above-referenced application are incorporated by reference herein and made part of this specification.

BACKGROUND

Field

This disclosure generally relates to the fields of radiography and computed tomography for medical and industrial applications.

Description of Related Art

Computed tomography (CT) allows reconstruction of a specific physical property of a 3-dimensional object and arranges and displays this reconstruction as an array of 2-dimensional cross-sectional or "tomographic" images of the object. Such reconstruction can be facilitated by appropriately configured X-ray or particle radiation that penetrates the object. Detection of such radiation and processing of such data can facilitate reconstruction of such 2-dimensional images.

Radiography allows the internal structure of a non-uniformly composed and opaque object to be viewed.

SUMMARY

Some embodiments disclosed herein relate generally to systems and methods of producing tomographic and/or radiographic images with high-energy electrons. Traditional computed tomography (CT) utilizes x-rays and measures line integrals of x-ray absorption, from which a 3D map of the linear photon attenuation coefficient of an inhomogeneous object can be reconstructed. In some embodiments, high-energy electrons that penetrate the object and travel on statistically predictable paths can be used in a novel approach to CT imaging. This technique can be called electron CT (eCT).

Traditional radiography includes directing a heterogeneous beam of x-rays toward an object and detecting the absorption of x-rays by the object to provide a superimposed 2D representation of the object's internal structures. In some embodiments, high-energy electrons can also be employed to produce one or more 2D projection images of an object's internal structures, such as, for example, living tissues in a patient. This technique can be called electron radiography (e-radiography).

An imaging system can use high-energy electrons at a low dose level to generate 3D computed tomography images and/or 2D radiographic images of living tissue and other objects. In some embodiments, a nozzle directs a source of high-energy electrons to the imaging target, and a detector system detects physical quantities of electrons that interact with the imaging target. In some embodiments, a computer system can calculate estimated paths taken by individual electrons within the imaging target, determine interactions between voxels of a digitized image of the imaging target and individual electrons, and reconstruct a digitized image of the imaging target based at least in part on the determined interactions between individual electrons and voxels. The imaging target can include but is not limited to living tissue, humans, pediatric patients, small animals, and other objects, such as those used in industrial applications.

The beam of high energy electrons can include electrons with typical energy levels greater than or equal to about 10 MeV, and in different embodiments can be different energy levels, up to and including 200 MeV or greater for certain applications requiring greater penetration power. The source of electrons can in some embodiments be controlled by a controller, which can perform functions including but not limited to emitting a series of one or more beams, and/or modifying the total dose of electrons to be delivered. In some embodiments, the total dose of electrons can range from 10 to 1000 per frame.

The detector system is highly sensitive and can detect physical quantities including but not limited to position, trajectory, and/or momentum. The detector system can in some embodiments be similar in at least some respects to the radiation detector described in U.S. Pat. No. 7,683,340 B2, titled: "Plasma Panel Based Radiation Detector," filed on Oct. 29, 2007, the entire contents of which are incorporated by reference and made a part of this application; and Publication No. US 2013/0284884 A1, titled "Plasma Panel Based Radiation Detector," filed on Mar. 22, 2013, the entire contents of which are incorporated by reference and made a part of this application. Other types of detectors can also be used. The detector system can in some embodiments be similar to those developed for pCT, as described in Publication No.: US 2011/0220794 A1, Titled: "Systems and Methodologies for Proton Computed Tomography," filed on Feb. 11, 2011, the entire contents of which are incorporated by reference and made a part of this application.

The computer system can be optionally coupled to a physical storage device. The computer system can in some embodiments comprise hardware processor resources and instructions that can be executed to cause the hardware processor resources to calculate estimated electron paths, determine interaction quantities, and reconstruct a 3D image.

The eCT reconstruction algorithm can in some embodiments allow use of the full discretization approach to the image reconstruction problem. This approach includes calculating estimated paths corresponding to actual paths taken by individual electrons within the object based on the recorded data. The interaction quantities and the estimated paths of the electrons are arranged such that the passages of the electrons through the object are represented as or representable as a system of equations $Ax=b$ where x is a distribution of a parameter associated with the object, b represents the interaction quantities of the electrons resulting from interactions along their respective paths in the object, and A is an operator that operates on x to yield b. The system of equations can be configured so as to have a plurality of solutions. In some embodiments, a solution is determined for the system of linear equations, the object parameter distribution is calculated based on the determined solution, and a computed tomography image of the object is generated based at least in part on the calculated object parameter distribution. The interaction quantity can in some embodiments describe attenuation of the intensity of the electron beam, and/or energy lost by an individual electron, and/or small-angle scattering, and/or large-angle scattering. The object parameter can in some embodiments correspond to propensity to attenuate the intensity of the electron beam and/or relative stopping power and/or scattering power and/or likelihood of a large-angle scattering event. The operator A includes information about the estimated paths of the electrons in the object. The elements of A can in some embodiments correspond to an estimated intersection length of a selected electron in a corresponding voxel, where the estimated intersection length is calculated as a straight-line approximation of the estimated path of the selected electron in the corresponding voxel so as to account for non-linearity of the actual paths of the electrons in the object and to allow the system of linear equations to have a plurality of solutions. The elements of A can in some embodiments correspond to likelihood that a selected electron underwent a large-angle scattering event in a corresponding voxel.

In some embodiments, the eCT reconstruction algorithm can use one or more algorithms selected from the class of iterative reconstruction algorithms. In certain embodiments, this method includes estimating an initial solution for the system of equations. The method can further include seeking a superior solution among the plurality of solutions by iteratively: calculating a feasible solution by perturbing the current solution, and designating the feasible solution as superior if the feasible solution has a superior characteristic for a quantity associated with a reconstruction of the object parameter distribution than the current solution. The quantity associated with a reconstruction of the object parameter distribution can comprise a total variation of the reconstructed object parameter distribution. The method can include calculating the object parameter distribution based on a selected superior solution.

In some embodiments, the solution can be determined by iteratively projecting perturbed elements of the discrete object vector x onto one or more hyperslabs. Perturbed elements of discrete object vector x are projected onto one or more hyperslabs by perturbing discrete object vector x using a perturbation corresponding to a gradient of a merit function; projecting the perturbed x onto the one or more hyperslabs using the projection algorithm, the projection algorithm being resilient to bounded perturbations; and calculating for the perturbed x a value of a merit function. The process can be repeated at least once to find a superior solution by using the current perturbed x as the vector to be perturbed, when the merit function value for the perturbed x is superior to the merit function for the discrete object vector x. The merit function can be associated with a reconstruction of the object parameter and comprises a total variation of the object parameter distribution.

eCT has commercial potential for medical applications, including but not limited to cardiac imaging, screening for lung cancer, screening for breast cancer, detection of kidney or gallbladder stones, and panoramic dental CT images. Imaging with high-energy electrons presents significant dose and resolution advantages over traditional imaging methods. For example, eCT cardiac screening can eliminate motion artifacts, improve temporal accuracy, and generate moving images of the living cardiac tissue. Further, eCT screening for breast cancer can be used to detect microcalcifications and can allow following women with a higher genetic risk of developing breast cancer with serial imaging, and eCT screening for lung cancer can be used to detect nodules and generate moving images of the living lung tissue. It is also possible to use contrast media, commonly used in x-ray imaging, to enhance the proposed method for applications in functional eCT (e.g., functional brain imaging), or cardiac imaging (e.g., ultrafast 3D coronary angiography).

BRIEF DESCRIPTION OF THE DRAWINGS

FIG. 2 shows simulated 150 MeV primary and secondary electron tracks in a 20-cm water slab and their cubic spline approximations.

DETAILED DESCRIPTION OF CERTAIN EMBODIMENTS

Figure 1:
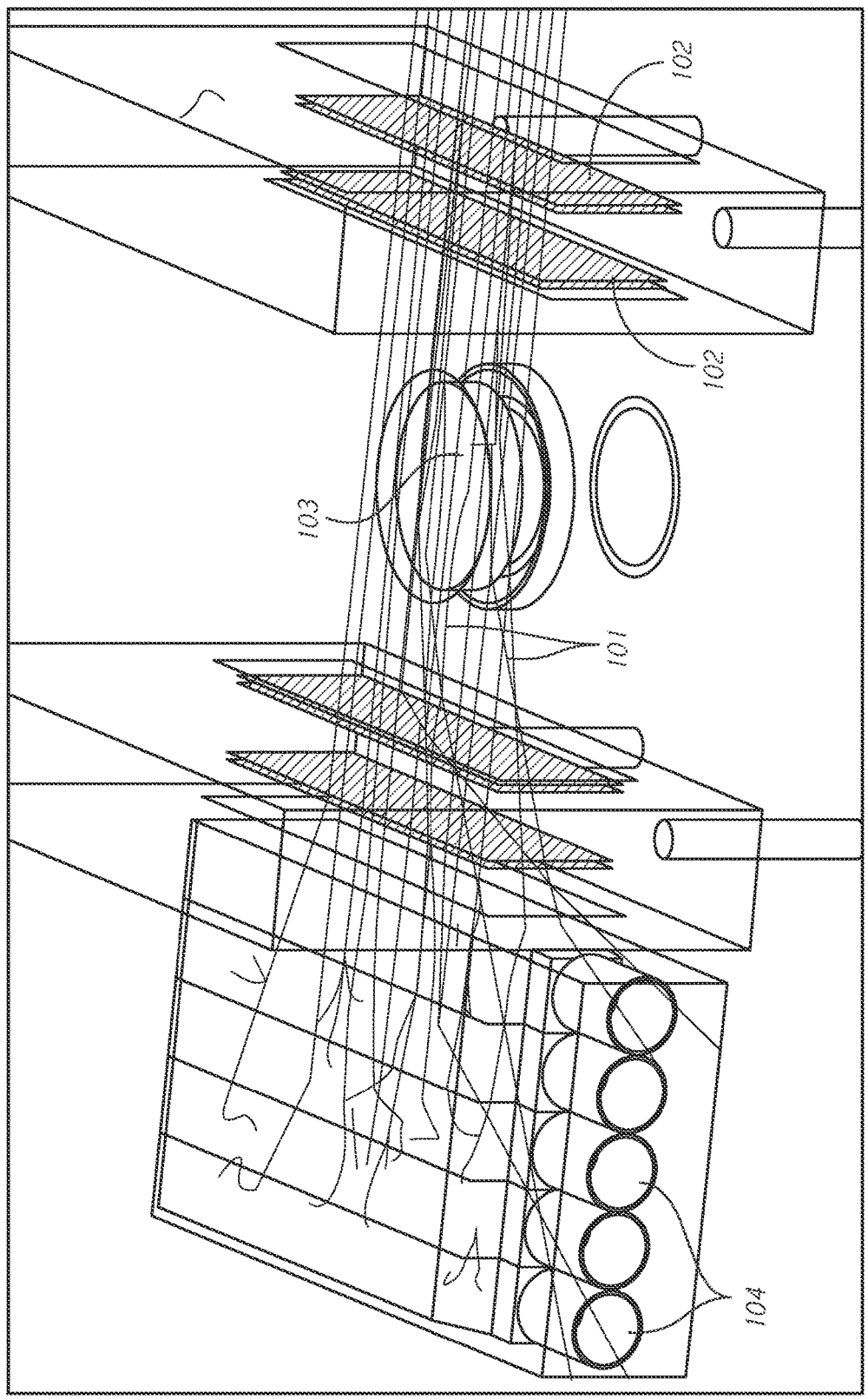
FIG. 1 shows a simulation of some implementations of high-energy electron CT with energy detectors.

Since the early 1970s, x-ray computed tomography (CT) has evolved into the preferred tomographic imaging modality using ionizing radiation. It is so widely used that diagnostic procedures with x-ray CT have become the main contributor to the annual exposure to ionizing radiation from diagnostic procedures in the United States and Europe. Though progress has been made in developing CT scanners that are more dose-efficient, introduction of new CT technology such as spiral CT and multidetector CT (MDCT) has further increased the annual dose from x-ray CT in the U.S. population over the last 15 years.

At present, it is felt that x-ray CT is approaching its technical limits, both in terms of the dose of ionizing radiation to patients and the achievable time resolution dictated by the need of mechanically rotating an x-ray source around the patient at high speeds. More recently it has been proposed to increase the speed of x-ray CT by moving an electron beam electromagnetically around a ring-like target producing x-rays. In this technique, called "electron beam CT" (EBCT), the x-ray source-point is swept electronically around the tungsten anode of the x-ray tube. EBCT still uses x-rays as the penetrating radiation. EBCT was developed specifically for the detection of calcium deposits in coronary arteries, and although EBCT heart scans offer some speed and dose advantages over MDCT scans, their clinical use is limited and not generally accepted.

In the early 1960s, Allan Cormack, one of the fathers of modern x-ray CT reconstruction, suggested heavy charged particles, such as alpha particles and protons, for medical tomographic imaging, allowing CT imaging with 5-10 times lower dose to the patient. The first applications of protons to radiography in the 1960s were based on energy-loss radiography. In the 1970s, researchers at CERN (the European Organization for Nuclear Research in Switzerland) explored the idea of using nuclear scattering of protons to obtain a three-dimensional reconstruction of an object. Under this approach, particle detectors detect scattering from a single exposure to a proton beam to reconstruct the trajectories of the incident and scattered particles. Due to minimal scattering in tissue, these investigators simply used the intersection of extrapolated entry and exit trajectories to determine the points of large-angle scattering. Though proton CT (pCT) technology is currently under extensive development, it is not likely to find diagnostic medical application because of the large size and prohibitive cost of the proton accelerators, unless a novel technology with inexpensive, compact accelerators will emerge, generating low-intensity, high-energy proton beams. None of these early researchers disclosed the potential of electrons for tomographic imaging.

Electrons, however, have been used for tomographic imaging at the sub-cellular level. Electrons have a long history of applications in imaging of microscopic specimens. For example, transmission electron microscopy (TEM) is used to image ultrathin samples, and scanning electron microscopy (SEM) is used to obtain a topographic image of a microscopic sample. Electron microscopes use a beam of electrons to create 2D projection images of samples. Electron tomography (ET) is a technique arising from TEM that images 3D structures on sub-micron scales by reconstructing a 3D image from a number of projections at different directions of view.

Despite the advent of pCT and ET technologies, the use of electrons for biological imaging has long remained limited to the sub-micron scale. Early researchers in electron tomography in the 1970s recognized that imaging biological samples with electrons leads to radiation damage of organic materials. High electron doses can, among other things, damage protein structures, whereas low electron doses create images with very poor spatial resolution. Imaging thicker samples requires higher electron doses in order to yield sufficient data for an image. Despite technological advances in electron tomography, electron doses required for biological samples thicker than about 1 micron still lead to unacceptable levels of radiation damage; and thus, specimen thickness for electron tomography is limited to about 1 micron.

Although protons have been used for CT imaging, electrons have thus far not been a viable alternative due to several important differences between protons and electrons. Electrons are about 2000 times lighter than protons. Due to this large difference in mass, electrons and protons interact with matter very differently. For example, and most significantly, electrons are much more susceptible to scattering than protons, and thus, in general, the curvature of the path of an electron is much greater than that of a proton. While the path of a proton is usually relatively linear, the path of an electron is curved and can even be zig-zagged. This scattering contributes to noise and poor spatial resolution, and can also require higher doses to obtain sufficient data for imaging. Electrons also undergo many more inelastic, or bremsstrahlung, interactions than protons, which contribute to breaking of chemical bonds (and thus, radiation damage), and noise. Applying the known principles of electron tomography to CT imaging would lead to an unacceptable balance between safe doses of radiation and adequate resolution. In particular, while a dose below 20 electrons per $Å^2$ is considered sufficiently non-damaging for a biological specimen, it creates noisy images. Current solutions being applied to electron tomography—staining, cryo-microscopy, and/or averaging images from multiple identical units—are impracticable for CT imaging.

However, the challenging characteristics of electrons may be overcome or beneficially utilized by the present invention. For example, in some embodiments, the greater sensitivity of electrons to scattering can be advantageous in making possible very low dose imaging and radiography, when coupled with a high energy electron beam and a highly sensitive detector system. Also, despite the greater scattering of electrons, high-energy electrons scatter only about twice as much inside tissue-equivalent media as protons with the same range, which in some embodiments can be accounted for by appropriate reconstruction algorithms. Thus, reasonable spatial resolution is possible with eCT. Moreover, larger scattering angles can in some embodiments be an advantage when imaging small variations in scattering characteristics using appropriate algorithms to reconstruct these characteristics. Further, electron beams are much easier to generate and accelerate than heavier charged particles, and require much less powerful steering magnets, which can be much faster and less expensive.

High-energy electron CT (eCT) couples a low dose of high-energy electrons with highly sensitive detectors to detect scattering and reconstruct 3D images at very low illumination of living tissue, and most significantly, humans. High-energy electrons with energies between about 20 MeV and about 200 MeV have water-equivalent ranges between 10 cm and 50 cm. The range of high-energy electrons can allow acquiring tomographic images of objects including but not limited to human extremities, head, body, small animals, or industrial objects for medical or other purposes, e.g., screening for security purposes at airports. For example, in some embodiments, the dose delivered by eCT for a full head scan with about 100 electrons per 1 $mm^2$ per frame and 180 frames can be of the order of sub-milli-Sievert (mSv), providing a dose advantage between 10 and 100 compared to x-ray CT. Depending on the object being imaged, eCT dose can be much lower, and can require as few as 1 frame, which provides much greater dose advantages.

Using electrons instead of protons for medical imaging is very attractive because, first, the dose advantage of protons over x-rays can be maintained or even improved, and, second, as opposed to large proton accelerators and even larger proton gantries required for proton imaging, compact electron accelerators and gantries are much easier to realize. Moreover, due to its compactness the electron accelerator can in some embodiments be integrated with or located directly on the gantry. The technology of compact high-energy (>50 MeV) electron sources has significantly advanced over the last 20 years and has reached the threshold of medical application. Voltage gradients of 100-150 MeV can now be realized in modern klystrons, and compact tabletop-size laser-driven electron sources are being developed. Thus, very compact electron radiography and CT machines could be built with today's technology.

In some embodiments a system for producing 3D images consists of or comprises: high-energy (about 10 MeV to about 200 MeV) electrons passing through the imaged object as a probe; a detector system registering the track and the integral of energy loss, or other physical quantities of each primary electron; and a computer system including imaging software using reconstruction algorithms.

Electron Source

A variety of sources of high-energy electrons can be used in various embodiments such as the following examples: high-gradient X-band linear accelerators, laser plasma accelerators, microtrons, and recirculating linacs.

There are a wide variety of accelerator types that can produce electron beams in the range of about 10 to about 200 MeV, and several recent advancements have reduced the size of such accelerators to the point where they can fit into a CT gantry. For example, high-gradient X-band linear accelerators can now routinely achieve gradients of 100 MeV/m with high reliability, enabling, in some embodiments, a 2-3 m long linac structure to be used in the eCT gantry. Laser plasma accelerators have shown the ability to create narrow energy-spread electron beams with energy >100 MeV, and in some embodiments can be used in an eCT system. The lasers used for such sources are steadily becoming more compact and less expensive. Finally, there are a number of recirculating accelerator topologies that can be used in some embodiments, such as microtrons and recirculating linacs.

These are typically heavier due to the use of bending magnets, but are well-proven and comparatively low-cost solutions for this energy range, and could be employed for an eCT system.

In some embodiments, a controller is configured to control the emission of electrons by the electron source. The controller can be configured to cause the electron source to emit a series of one or more electron beams to generate one or more frames. The controller can also optionally be configured to modify the energy level, dose, and/or other physical quantities of the electron beam(s). For example, for each frame, the beam can be configured to deliver a dose of less than or equal to about 100 electrons per square millimeter, less than or equal to 150 electrons per square millimeter, less than or equal to 200 electrons per square millimeter, less than or equal to 500 electrons per square millimeter, less than or equal to 1000 electrons per square millimeter, greater than or equal to 80 electrons per square millimeter, greater than or equal to 50 electrons per square millimeter, greater than or equal to 30 electrons per square millimeter, greater than or equal to 10 electrons per square millimeter, between about 50 and 500 electrons per square millimeter and/or between any of the other foregoing values. The controller can thus be configured to modify the total dose of electrons, by configuring the dose per beam, and the number of beams.

In some embodiments, the electron source can be movable relative to the imaged object. For example, the electron source can be rotatable around the imaged object. This mobility of the electron source can improve spatial resolution and accuracy of the 3D image by providing different angles of view.

In some embodiments an electron accelerator can be constructed as a stationary multiport machine surrounding the imaged object, thus eliminating any movable parts from the system and obtaining high sweeping speeds. The latter design can provide a speed-up of CT, which can be of value for, among other things, cardiac applications. In turn, the short scanning time allows CT imaging of intrinsically fast processes such as heart motion.

Detector System

The high detection efficiency of modern tracking detectors (near 100%) to charged particles can contribute to a significant dose advantage compared to x-ray CT.

The detector system of a high-energy eCT scanner can in some embodiments record the history of individual primary electrons in real time. The recorded data regarding each primary electron can include one or more of: initial kinetic energy; an electron's entry coordinates; exit coordinates; entry directions; exit directions; the residual energy of primary particles; and the residual energy of any recorded secondary particles. In some embodiments, the data recorded from the detector system can be used to derive quantities including but not limited to position, trajectory, and/or momentum of individual electrons.

The detector system of a high-energy eCT scanner can in some embodiments utilize a detector with low integral density along the direction of the incident electron beam. In some embodiments, the water equivalent thickness of the detector can be less than or equal to 10 millimeters. A lower integral density detector decreases the likelihood of scattering interactions between the electrons and the atoms of the detector, which contribute to noisiness in the image data.

The detector system of a high-energy eCT scanner can in different embodiments have different geometries. For example, such geometries can include but are not limited to a flat panel, a ring around the imaged object, or the capability of being bent into different shapes. Flexible geometries permit detection of electrons across a greater spatial range and improved data recordation.

The detector system of a high-energy eCT scanner can in some embodiments be similar to those developed for pCT, as described in Publication No.: US 2011/0220794 A1, Titled: "Systems and Methodologies for Proton Computed Tomography," filed on Feb. 11, 2011, the entire contents of which are incorporated by reference and made a part of this application. In some embodiments the system can utilize a detector comprising front and rear Si micro-strip telescopes and a plastic-scintillating energy detector as the residual energy measurements.

The detector system of a high-energy eCT scanner can in some embodiments include front and/or rear tracking detectors that register physical quantities, including but not limited to the entry and exit points and directions, of electrons traversing the scanned object on a particle-by-particle basis. This system can in some embodiments include a rear detector, with no front detector, if the entry point and direction of the electrons are known with sufficient accuracy, e.g., by scanning pencil-beam across the object. This system can in some embodiments be a detector ring surrounding the object for more than one frame. The detector can in some embodiments be similar to the radiation detector described in U.S. Pat. No. 7,683,340 B2, titled: "Plasma Panel Based Radiation Detector," filed on Oct. 29, 2007, the entire contents of which are incorporated by reference and made a part of this application; and Publication No. US 2013/0284884 A1, titled "Plasma Panel Based Radiation Detector," filed on Mar. 22, 2013, the entire contents of which are incorporated by reference and made a part of this application. In some embodiments the detector can utilize plasma panel sensors with a dense array of pixels that operate independently as Geiger-Mueller-type counters of electrons.

The detector system of a high-energy eCT scanner can in some embodiments be the combination of a particle energy detector and an electron entry and/or exit location detector.

Reconstruction Algorithm

The eCT reconstruction algorithm can in some embodiments allow use of the full discretization approach to the image reconstruction problem. This approach includes calculating estimated paths corresponding to actual paths taken by individual electrons within the object based on the recorded data, the estimated path providing an estimate of the actual path. The interaction quantities and the estimated paths of the electrons are arranged such that the passages of the electrons through the object are represented as or representable as a system of equations $Ax=b$ where $x$ is a distribution of a parameter associated with the object, $b$ represents the interaction quantities of the electrons resulting from interactions along their respective paths in the object, and $A$ is an operator that operates on $x$ to yield $b$. The interaction quantity can in some embodiments describe small-angle scattering and/or large-angle scattering. The object parameter can in some embodiments correspond to relative stopping power and/or scattering power and/or likelihood of a large-angle scattering event. The operator $A$ includes information about the estimated paths of the electrons in the object. The system of equations can be configured so as to have a plurality of solutions. In some embodiments, a solution is determined for the system of linear equations, the object parameter distribution is calculated based on the determined solution, and a computed tomography image of the object is generated based at least in part on the calculated object parameter distribution.

The eCT reconstruction algorithm can further utilize application of duly developed algorithms from the class of iterative reconstruction algorithms. The method includes estimating an initial solution for the system of equations. The method further includes seeking one or more feasible solutions among the plurality of solutions, with each feasible solution obtained by perturbing an existing solution and having a superior characteristic for a quantity associated with a reconstruction of the object parameter distribution as compared to another solution obtained without the perturbation of the existing solution. The method further includes calculating the object parameter distribution based on a selected one of the one or more feasible solutions.

Most Likely Path Reconstruction

The eCT reconstruction algorithm can in some embodiments utilize a most likely path (MLP) concept. In some embodiments the MLP for eCT can be similar to the concepts developed for pCT, as described in Publication No.: US 2011/0220794 A1, Titled: "Systems and Methodologies for Proton Computed Tomography," filed on Feb. 11, 2011, the entire contents of which are incorporated by reference and made a part of this application. The eCT reconstruction algorithm can in some embodiments be implemented on modern, high-performance computing hardware that transforms the detector data flow into a time series of 3D image sets of the object with gray scale values depending on the object electron density and atomic composition, thus providing the internal object structure as a function of time (4D CT). The short time scale in which data can be acquired and processed with eCT, allows imaging of moving objects such as the human heart with high time resolution.

A Geant4 detector simulation toolkit was used to perform a preliminary study testing the eCT concept with cone beams of high-energy electrons passing through a water phantom and a scanner. The scanner comprises front and rear Si micro-strip telescopes and a plastic-scintillating energy detector as the residual energy measurements. The simulated set-up is shown in FIG. 1. FIG. 1 shows a parallel 2D beam of 100 MeV electrons, line 101, the Si telescope planes, line 102, the 15 cm-thick water phantom surrounded by a 0.5-cm thick acrylic shell, line 103, and the 5 stage energy/range detector, line 104. As in FIG. 1, the electrons can in some embodiments be detected in all tracking planes and then their energy (or residual range) measured in the energy/range detector. Both residual range and amount of scattering (angular and spatial displacement) can provide integrated information about the target object from which a 2D or 3D image can be reconstructed.

Individual tracks of 150-MeV electrons that only underwent elastic Coulomb scattering can be reconstructed with a spatial resolution of the order of 1 mm at the center of a 20-cm water phantom by, in some embodiments, using a 3D cubic spline approximation. Further improvement can in some embodiments be provided with the MLP formalism as already developed for pCT reconstruction, as described in Publication No.: US 2011/0220794 A1, Titled: "Systems and Methodologies for Proton Computed Tomography," filed on Feb. 11, 2011, the entire contents of which are incorporated by reference and made a part of this application. The resolution obtained with the simplified cubic-spline approach is only about a factor two worse than the path resolution for pCT, which is about 0.5 mm for the same water phantom and a 200 MeV proton beam. This unexpected result can be explained by the relatively small difference in the particle deflection due to multiple scattering for protons and electrons. The deflection is inversely proportional to the product of particle momentum and velocity, and for 200-MeV protons this product is less than factor 2 larger than that of 150-MeV electrons. A few examples of simulated electron tracks through the 20-cm water slab and their reconstructed paths are shown in FIG. 2(a).

Figure 2B:
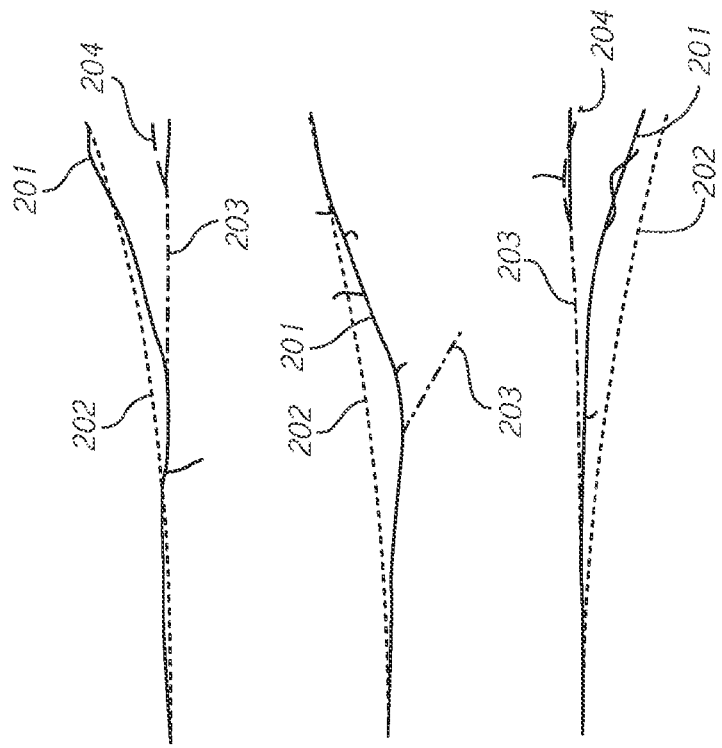
FIG. 2B simulates more complicated tracks.
Figure 2A:
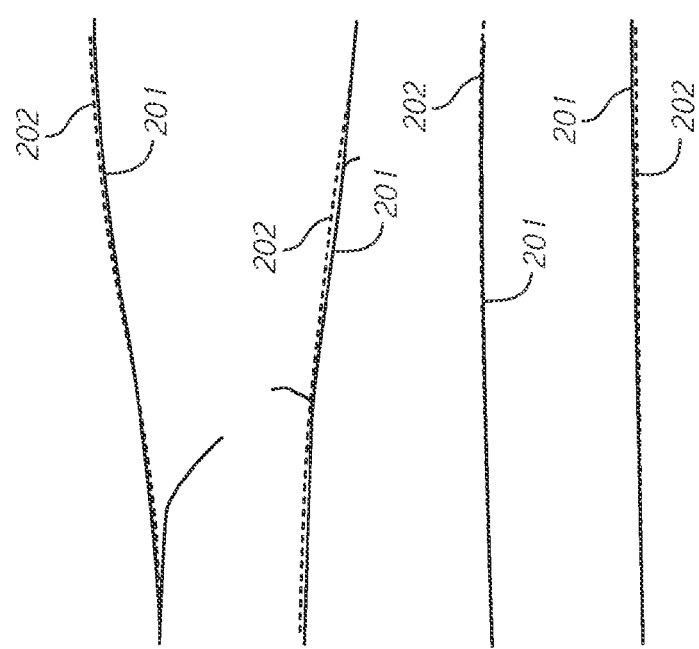
FIG. 2A simulates tracks undergoing elastic Coulomb scattering.

FIG. 2 shows simulated 150 MeV primary and secondary electron tracks, lines 201, in a 20-cm water slab and their 3D cubic spline approximations, lines 202. Note that the vertical axis of FIG. 2 is magnified two times relative to the horizontal axis. FIG. 2A shows that tracks only undergoing elastic Coulomb scattering 201 can be fitted well by their spline approximation 202 to a resolution of about 1 mm FIG. 2B shows more complicated tracks with additional high-energy bremsstrahlung photons, lines 203, and electron-positron pairs, lines 204. The spline-approximated tracks 202 deviate significantly from the original tracks 201, 203, and 204 in these cases. The bottom right electron underwent additional scattering in the downstream tracker, leading to a mismatch between the extrapolated simulated track and the true track at the exit from the water slab.

The Geant4 detector simulation toolkit can provide detailed computer models of the new eCT modality by simulating high-energy (10 MeV to 200 MeV) electron beams and realistic phantom and detector set-up geometries to study in detail the characteristics, types and frequency of physical interaction processes in the scanner hardware and in the imaged object. These simulations can be compared with well-known electron transport properties (energy loss, ranges, bremsstrahlung spectra, pair production, etc.) and existing experimental data. The validated Geant4 model of the (virtual) eCT scanner can be used to simulate complete CT scans of anthropomorphic head and body phantoms to produce realistic data.

A reconstruction methodology can in some embodiments incorporate the analysis and categorization of particle tracks according to underlying physical processes of high-energy electrons and their characteristics, such as collision and radiative energy losses of the primary electrons, scattering angle distributions, and probabilities of rare interaction processes. Simulations can be performed in water, the standard reference material in medical physics, and standard human tissues (soft tissue and bone). In some embodiments, the preparation of the MLP reconstruction involves classifying primary electron tracks according to the underlying physical processes. For example, in some embodiments a simple approximation using cubic splines can be utilized for the MLP if electrons underwent only small-angle scattering, as shown in FIG. 2A, whereas a different and more advanced model can be used in case of electron tracks with large bremsstrahlung events leading to a relatively large deflection of the track, as shown in FIG. 2B.

In some embodiments, systems, methods, components, and/or approaches developed for proton computed tomography, such as, for example, those described in US Patent Application Publication No. 2011/0220794 A1, titled "Systems and Methodologies for Proton Computed Tomography," filed Feb. 11, 2011, the entire contents of which are incorporated by reference herein and made a part of this application, can be utilized for eCT. From the residual energy of individual particles one can infer, for example via a calibration procedure, the water-equivalent path length (WEPL) of each particle that would have led to the same average energy loss as that observed if the particle had intersected a slab of water. Mathematically, the energy-loss WEPL equals the integral of relative stopping power (RStP) with respect to water, which is practically energy-independent and, therefore, a characteristic tissue property that describes the average energy loss per particle relative to water as the reference material.

In order to reconstruct RStP, one can estimate the MLP. For eCT, an assumption can be made in some embodiments that the electrons are scattered in water with a probability density distribution that has a Gaussian approximation. Thus, the deflection of the particle relative to its original direction and location can in some embodiments be described by a bivariate Gaussian distribution and an MLP can be inferred based on a Bayesian approach. A similar approach can in some embodiments be used for the measurement of scattering WEPL, i.e., an equivalent path length in water that would on average lead to the observed scattering angle variance of the particle upon exit. The scattering WEPL equals the integral of relative scattering power with respect to water, from which the RStP can be reconstructed.

Figure 3:
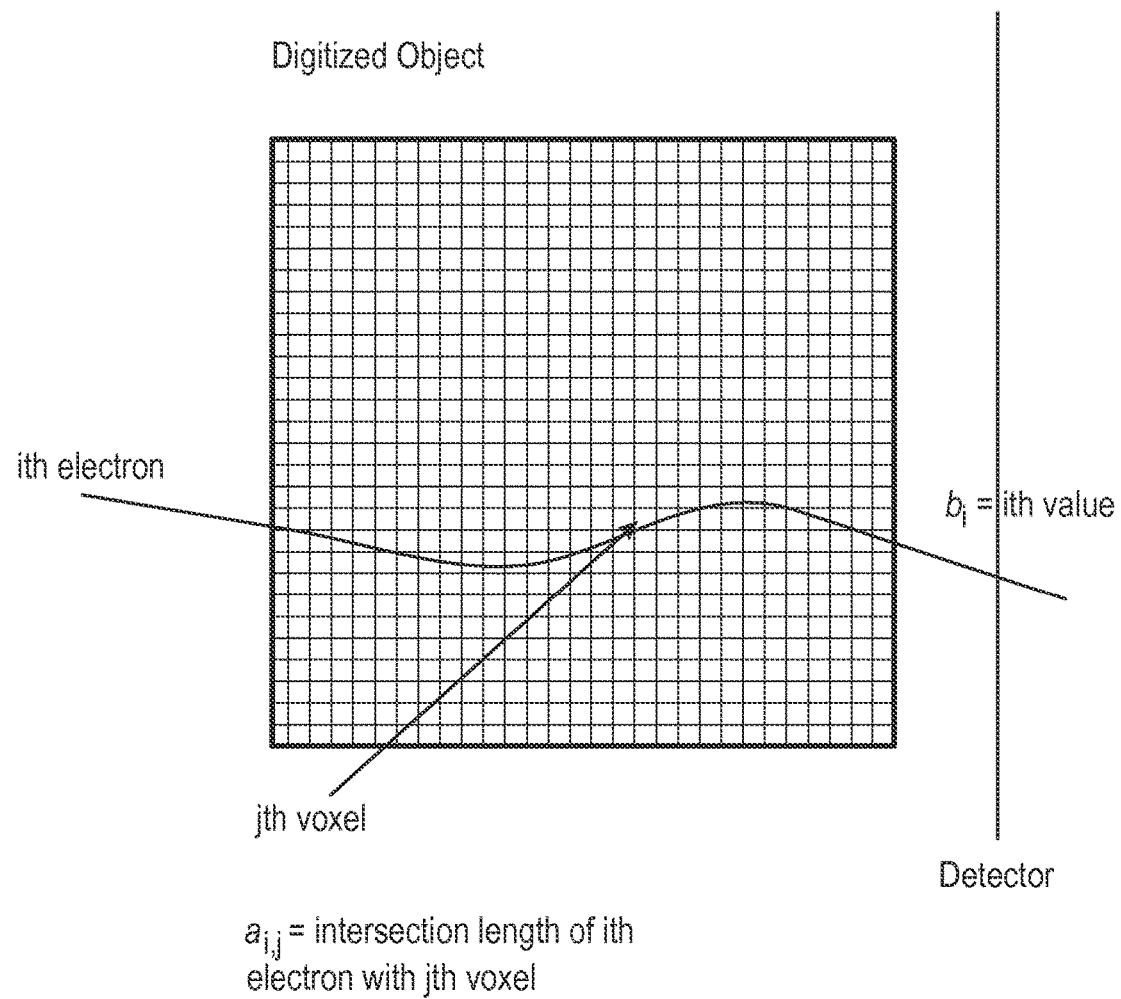
FIG. 3 shows a formation of a matrix using the most likely path (MLP) of an electron.

In some embodiments, the MLP concept can be utilized in the discretization approach to image reconstruction. FIG. 3 shows the formation of matrix A, as in some embodiments, using the MLP, where matrix element $a_{i,j}$ corresponds to the intersection length of the i-th particle with the j-th voxel. The object can in some embodiments be digitized from the outset, forming an m-dimensional x-vector of unknown stopping power values of the object. The MLP can in some embodiments also be digitized and expressed as a matrix row vector $\{a_{i,j}\}$ where i is the index of the electron (i= 1, 2 ... n) and j is the object voxel index (j=1, 2 ... m). The n×m matrix A composed in some embodiments of these vectors is the "system matrix" of the linear system of equations: Ax=b, where the elements $a_{i,j}$ correspond to the length of intersection (chord length) of the i-th particle history's path with the j-th voxel, x is the unknown m-dimensional image vector, and b is the n-dimensional vector, whose elements b correspond to the integral RStP, i.e., the RStP measured along the i-th electron path.

Charged particles being deflected in the nuclear Coulomb field of the target nuclei emit radiative energy (bremsstrahlung). For relativistic particles, the bremsstrahlung is inversely proportional to the particle mass and, therefore, is much more important for light particles (electrons) than for heavier particles (protons). The energy transfer due to bremsstrahlung has an inversely cubic dependence on the impact parameter (distance between projectile and target nucleus). This means that there will be relatively rare events of large energy transfer and deflection that can in some embodiments be treated differently from the "continuous" small energy loss and angular deflections of most electrons.

In some embodiments, the methodology for most likely path reconstruction can employ track-pattern recognition to classify electron tracks with no, single, or multiple large-angle bremsstrahlung scattering events. In some embodiments those tracks with two or more large-angle scattering events can be excluded from the reconstruction. In some embodiments, a probabilistic model of the inflection point can be developed for events with single large-angle scattering on the path (as in FIG. 2B), and the MLP segments before this point can be modeled with the MLP approach. For events with continuous energy loss and scattering (as in FIG. 2A), established MLP methods or approximations (e.g., cubic splines) can in some embodiments be employed.

In some embodiments, the accuracy of the most likely path calculation can be greatly improved when the boundary of the object relative to the trackers is known. The object boundary could be inferred, for example, from a laser-based optical surface scan. Those scanning systems have been developed for patient positioning tracking and are commercially available.

3D Electron Scattering Reconstruction

The eCT reconstruction algorithm can in some embodiments utilize the scattering power, i.e., the ability of each voxel in the object to scatter electrons of the imaged object based on imaging with high-energy electrons. The scattering power of tissues in patients or materials in other objects of interest can be very different depending on the atomic number (Z) of the elements comprising the object and the local density variation. In medical applications, this will allow distinguishing tissues based on the presence of calcium, for example, or other high Z materials or materials that are soft tissues but are embedded in a low-density material such as lung. Examples of clinical applications include detection of calcifications in breast tumors, which is currently performed with x-ray mammography, detection of early stage lung cancer in persons at high risk due to an intensive smoking history, early detection of coronary artery disease, or detection of kidney and gallbladder stones. It is also possible to use contrast media, commonly used in x-ray imaging, to enhance the proposed method for applications in functional eCT or cardiac imaging, for example ultrafast 3D coronary angiography.

In some embodiments, the scattering reconstruction is based on the reconstruction of the location of voxels where electrons scatter at relatively larger angles, which occurs with higher probability in voxels with higher Z and/or density than the surrounding voxels. Reconstructing the relative number of such large-angle scattering events, normalized to the number of electrons crossing the voxel, will lead to good contrast discrimination between voxels of different densities and Z number. From the electron entry and exit locations and directions, one can estimate track segments, assuming that the object is composed of a predominant material or tissue (e.g., soft tissue in the case of female breast). In some embodiments, the difference between exit and entry directions defines the electron scattering angle, and, if this angle is larger than a threshold value that is determined by the thickness and assumed composition of the object and the predominant multiple Coulomb scattering composition, one can assume that a single large scattering event has occurred. The most likely location of this event can be inferred by the reconstructed track segments into the scanned object. These two straight lines will generally not intersect in three dimensions, but will have a depth of closest approach given by a plane perpendicular to the entry direction. The object voxel located in this plane that is intersected by the reconstructed track segments will be assigned the mostly likely location for the large-angle scattering event. Scoring the number of such events in each voxel allows a 3D reconstruction of electron scattering power, which will have the highest spatial resolution in the plane perpendicular to the electron beam direction.

Figure 4:
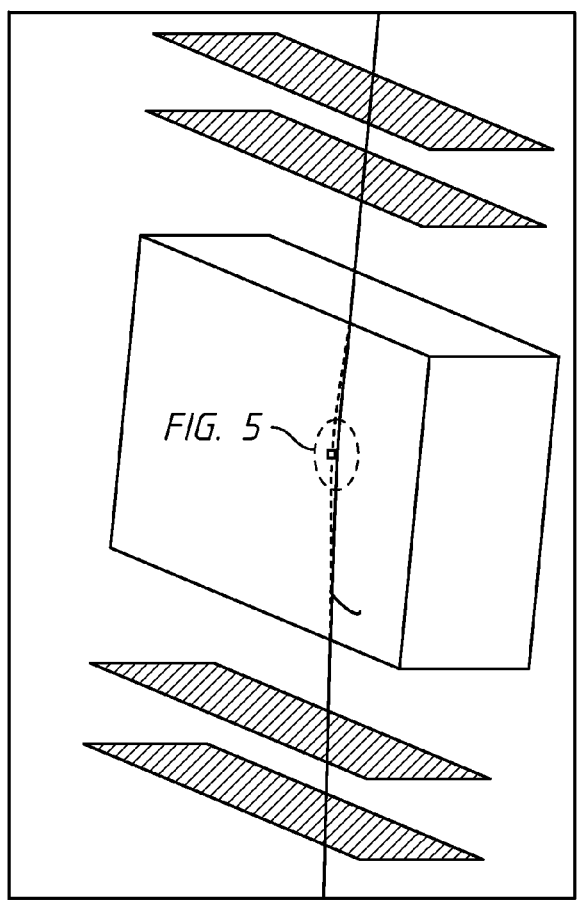
FIG. 4 shows a simulation of some implementations of high-energy electron CT with entry and exit position detectors.
Figure 5:
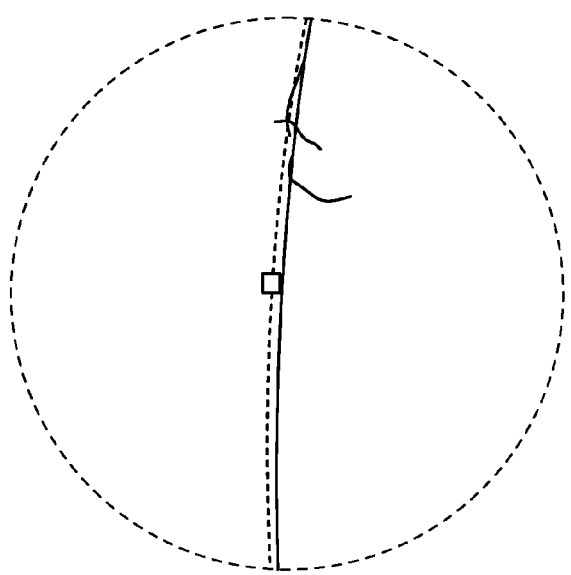
FIG. 5 shows a simulated reconstruction of a scattering point.

FIG. 4 shows a conceptual representation of an eCT apparatus utilizing 3D electron scattering reconstruction, as represented by a Geant4-based Monte Carlo simulation model. The figure shows a single electron tracked through the detectors and the object. Two pairs of 2D position-sensitive detectors, with one pair located before and the other after the phantom, register track segments of an individual electron that can be used to reconstruct the location of large-angle scattering. The insert (FIG. 5) shows the detail of the scattering point reconstruction.

In some embodiments, the scattering reconstruction approach can be utilized in the discretization approach to image reconstruction. A matrix C can be formed for a digitized image of the living tissue wherein matrix element $c_{i,j}$ corresponds to the likelihood that the $i^{th}$ electron underwent a large-angle scattering event in the $j^{th}$ voxel of the digitized image. The object can in some embodiments be digitized from the outset, forming an m-dimensional x-vector of unknown large-angle scattering powers of the object. The scattering power can in some embodiments also be digitized and expressed as a matrix row vector $\{c_{i,j}\}$ where i is the index of the electron (i=1, 2 . . . n) and j is the object voxel index (j=1, 2 . . . m). The n×m matrix C composed in some embodiments of these vectors is the "system matrix" of the linear system of equations: Cx=b, where the elements $c_{i,j}$ correspond to the length of intersection of the $i^{th}$ particle history's path with the $j^{th}$ voxel, x is the unknown m-dimensional image vector, and b is the n-dimensional vector, whose elements $b_i$ correspond to the large-angle scattering measured along the $i^{th}$ electron path.

In some embodiments, the scattering reconstruction method allows 3D reconstruction with just one frame. In other embodiments, multiple frames can further improve on image quality.

In some embodiments, the most likely path reconstruction can be combined with the scattering reconstruction. The most likely path approach improves on the accuracy of the scattering reconstruction compared to solely relying on tracks extrapolated from electron entry and exit locations. The mostly likely path reconstruction and scattering reconstruction can together be applied to the discretization calculation. The interaction quantity can describe small-angle scattering and large-angle scattering of an electron during its passage through the object. The object parameter can correspond to the relative stopping power of each voxel, and to the likelihood of a large-angle scattering event occurring in each voxel.

Attenuation Reconstruction

The eCT reconstruction algorithm can in some embodiments utilize the integral of density along the path of each electron based on the intensity of the electron beam exiting the imaged probe to generate a 2D attenuation radiograph. This is possible, because a significant fraction of incoming electrons is absorbed in the scanned object, particularly in high-Z or high-density voxels, thus producing "shadows" in image regions where electrons crossed those voxels. In some embodiments, the 2D attenuation radiograph can be reconstructed, for example, by counting the most likely paths intersecting each voxel, excluding those paths that were marked as large-angle scattering events. The count of paths in each voxel can be normalized to the number of incoming electron tracks intersecting the voxel in order to take into account non-uniform intensity of the incoming electron beam. Summing up the normalized voxel counts along voxel columns in the direction of the incoming electron beam results in a 2D attenuation radiograph.

In some embodiments, the 2D attenuation radiographs can be combined to reconstruct time-resolved 2D attenuation radiography with much lower radiation exposure as compared to conventional imaging methods. This is possible because the 2D attenuation radiograph can be reconstructed in quasi-real time, resulting in very high time resolution of changes in attenuation.

In some embodiments, 2D attenuation radiographs can be combined to reconstruct the attenuation coefficients with a standard algorithm for tomographic reconstructions from projections, e.g., the filtered back projection algorithm. The voxel sum of attenuation coefficients may also be expressed relative to what would be expected for a water object of the same physical thickness as the scanned object along the voxel column. This will result in an electron attenuation CT similar to the standard x-ray CT.

In some embodiments, the attenuation radiograph can be combined with the most likely path reconstruction and/or the 3D scattering reconstruction. For example, in some embodiments, the 2D attenuation radiography can be utilized to locate the contours of the imaging target. The knowledge of the location and contours of the imaging target can be utilized to improve spatial resolution and accuracy of the 3D reconstruction.

Additional Options for Reconstruction

In some embodiments, inherently parallel block-iterative and string-averaging projection optimization algorithms can optionally be used. Those parallelizable algorithms may not degrade image quality and in some embodiments such algorithms can require fewer cycles to achieve minimum relative error. Some embodiments incorporate superiorization schemes that use iterative projection methods and allow superiorization of a target (merit) function such as total variation (TV) or others. The superiorization methodology (SM) can in some embodiments allow the conversion of a feasibility-seeking algorithm, designed to find an c-compatible solution of the constraints, into a superiorized algorithm that inserts objective function reduction steps into the feasibility-seeking algorithm without ruining the guaranteed feasibility-seeking nature of the algorithm. This methodology can in some embodiments be computationally efficient and useful in terms of the image reconstruction application.

In some embodiments, additional optional reconstruction methods could be applicable, for example Kalman filter, pattern recognition, or machine learning techniques.

In some embodiments, if large discrete bremsstrahlung events negatively impact the image reconstruction quality, these events can be excluded from reconstructions. Any resulting loss of dose efficiency can be relatively small because those events are relatively uncommon, especially for small (e.g., pediatric) patients that require lower initial electron energies.

Other Features of the Disclosed Embodiments

Figure 6:
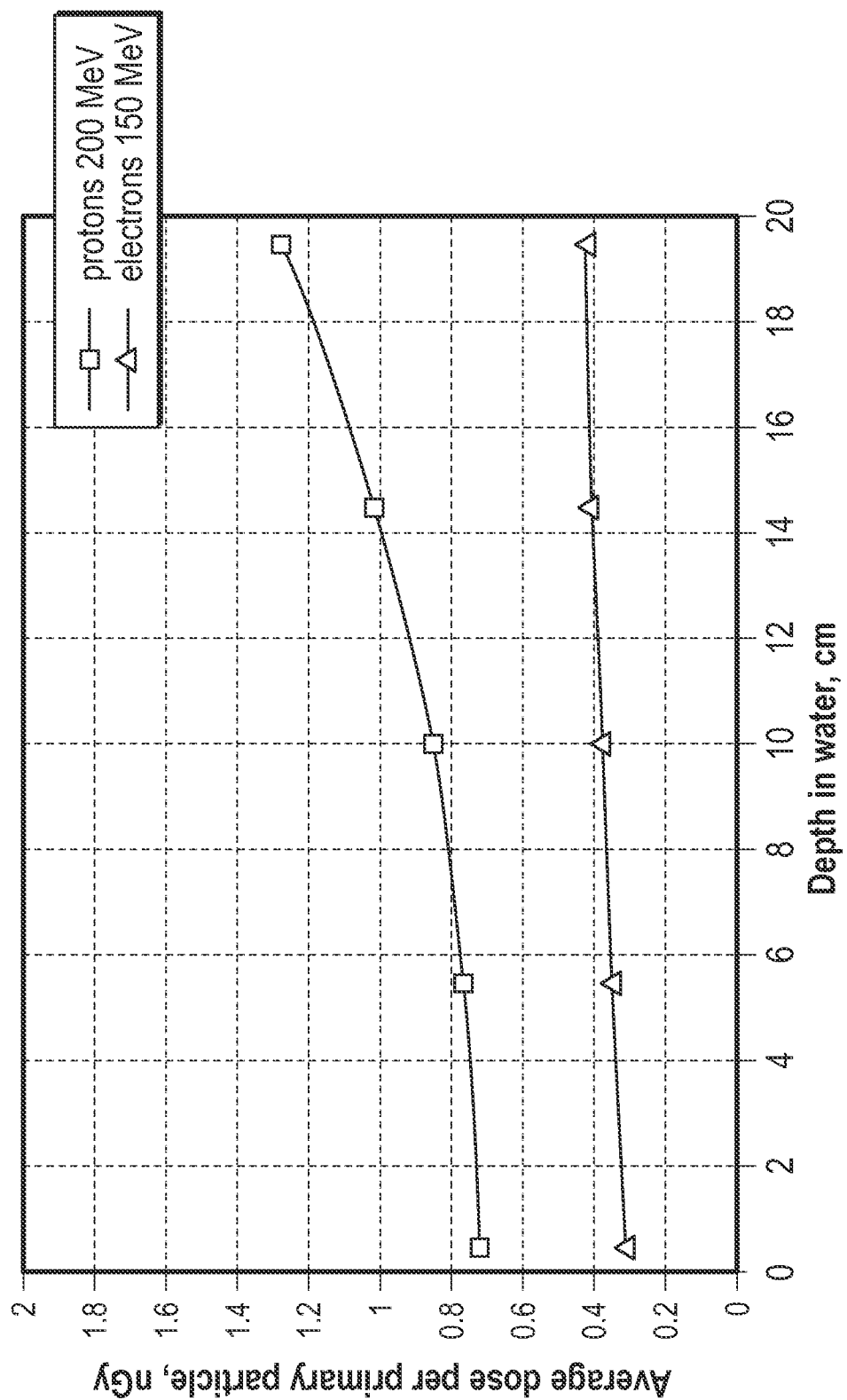
FIG. 6 shows a graph of average dose deposited per particle in a 1 cm-layer of water by 200 MeV protons and 150 MeV electrons traversing a 20-cm water slab.

The dose delivered per primary particle to the imaged object can in some embodiments be about 2.5 times lower for eCT than for pCT, as shown in FIG. 6. FIG. 6 shows a graph of an average dose deposited per particle in a 1 cm-layer of water by 200 MeV protons and 150 MeV electrons traversing a 20-cm water slab. High-energy eCT can in some embodiments provide an image quality comparable to that of pCT at a similar or even lower delivered dose. The radiobiological effectiveness of relativistic electrons is lower than that of protons, and electrons produce significantly less nuclear interactions and hence less neutrons and highly ionizing nuclear fragments in the imaging object, so eCT can have a radiation quality factor equal to unity, i.e., eCT can be biologically equivalent to x-ray CT. The dose delivered by eCT, e.g., for a full head scan with about 100 electrons per 1 $mm^2$ per frame and 180 frames can be-milli-Sievert (mSv), providing a dose advantage between 10 and 100 compared to x-ray CT. In some embodiments, each beam can provide a small dose of electrons to the tissues being imaged. For example, for each frame, the beam can deliver a dose of less than or equal to about 100 electrons per square millimeter, less than or equal to 150 electrons per square millimeter, less than or equal to 200 electrons per square millimeter, less than or equal to 500 electrons per square millimeter, less than or equal to 1000 electrons per square millimeter, greater than or equal to 80 electrons per square millimeter, greater than or equal to 50 electrons per square millimeter, greater than or equal to 30 electrons per square millimeter, greater than or equal to 10 electrons per square millimeter, between about 50 and 500 electrons per square millimeter and/or between any of the other foregoing values. Even larger dose advantages can be expected for imaging smaller objects, such as extremities and pediatric patients. Further, in some embodiments, as few as 1 frame is sufficient for reconstruction of a 3D image, providing an even greater dose advantage.

In some embodiments, the eCT imaging system can be combined with a contrast media, commonly used in x-ray imaging, to enhance the proposed method for applications in functional eCT (e.g., functional brain imaging), or cardiac imaging (e.g., ultrafast 3D coronary angiography). For example, in some embodiments, a contrast agent can be injected into the patient prior to eCT imaging. The contrast agent can increase differentiation between abnormal and normal tissue to enhance resolution of the imaging target. The contrast agent can also be utilized in combination with one or more eCT image reconstructions to reconstruct a three dimensional moving image of the living tissue.

Design specifications for an eCT scanner can in some embodiments address one or more of any of the following parameters:

Spatial and contrast detail resolution requirements of eCT images.

Quantitative accuracy of density measurements.

Dose-efficiency of a scanner that meets image quality requirements.

Time resolution requirement.

Scanner cost limit and life-time requirements.

Required electron beam source parameters, such as energy range, energy spread, current, repetition, etc.

Rate, beam size and divergence, as well as stability of these parameters.

Besides the performance evaluation of a system, defining these parameters can in some embodiments allow a virtual optimization of the detector parameters and choice of available accelerator technology.

Commercial Potential

The proposed method of electron CT and 3D radiography with electron beams has great commercial potential for medical and industrial applications. Three non-limiting examples for future medical applications are given below.

Cardiac Imaging: 3D volumetric imaging simultaneously covering larger volumes of the heart or the entire heart combined with improved temporal resolution will allow imaging with much lower radiation exposure and better temporal accuracy as compared to conventional imaging with x-ray CT. The proposed method can be easily integrated into the existing work flow of cardiac imaging, replacing cardiac CT with more compact equipment and less radiation exposure to patients and personnel.

For example, in some embodiments, high-energy electrons are directed to cardiac tissue, and a detector system is configured to detect physical quantities of the electrons traversing the cardiac tissue, such that a computer system can reconstruct a 3D image that minimizes motion artifacts. More specifically, in some embodiments, only one or a small number of frames can collect sufficient data to generate a 3D image, when a scattering reconstruction algorithm is utilized, independently or in combination with a most likely path reconstruction. Imaging data is thus obtained during a very short period of time, which minimizes motion artifacts and increases temporal accuracy in the reconstructed images.

In another embodiment of electron CT applied to cardiac imaging, frames may be taken at an angular rate asynchronous to the measured cardiac cycle to obtain image data; and an image can be reconstructed from chronologically discontinuous segments of the image data. The reconstructed image is representative of a selected portion of the cardiac cycle, for example, a relatively quiescent portion.

In another embodiment of electron CT applied to cardiac imaging, multiple frames may be taken at intervals shorter than one cardiac cycle; and the frames can be reconstructed to form a time-resolved 3D image of the living cardiac tissue.

The resulting images are useful in medical applications requiring high temporal resolution images, for example, calcification scoring, which requires a high-resolution image of a relatively still heart. 3D cardiac imaging may also be beneficial for a variety of other medical applications, for example, by enabling planning for minimally invasive cardiac surgery.

Screening for Breast Cancer: Breast screening with low-kV x-ray mammography, while having a recognized benefit, also has significant disadvantages, in particular the risk of causing additional cancers of breast cancers due to radiation exposure. The proposed method applied to screening of breast cancer in pre-menopausal breast tissue would maintain detection efficiency but significantly reduce dose, possibly by more than one order of magnitude. This would allow following women with a higher genetic risk of developing breast cancer with serial imaging. The hallmarks of malignant breast lesions are areas of higher density within the normal breast or areas of calcifications.

For example, in some embodiments, high-energy electrons are directed to breast tissue, and a detector system is configured to detect physical quantities of the electrons traversing the breast tissue, such that a computer system can reconstruct a 3D image with high spatial resolution of areas of increased density and/or areas with high Z materials, such as calcium. The breast eCT scanner can optionally include an apparatus for supporting the patient in a prone position, wherein the apparatus includes at least one aperture for receiving a patient's pendulant breast, such that one or two breasts are exposed to the electron beam.

The breast eCT scanner provides a significant dose advantage over traditional methods of breast imaging. Electron beams can be configured to deliver a total dose of less than or approximately equal to 1000 electrons per square millimeter of breast tissue to be screened. In some embodiments, only one frame can collect sufficient data to generate a high-resolution 3D image, when a scattering reconstruction algorithm is utilized independently or in combination with a most likely path reconstruction. In other embodiments, multiple frames can further improve on image quality, for example by enhancing resolution of microcalcifications. As used herein with respect to a stated quantity or number, the terms "approximately equal to" or "about" mean that an actual quantity or number can be within 5% of the stated quantity or number.

In some embodiments, image data corresponding to the breast tissue may be utilized by the computer system to generate quasi-real-time images, which may be displayed on a quasi-real-time basis, thereby facilitating biopsy, surgical, and/or other treatment procedures.

Screening for Lung Cancer: Large screening studies with low dose helical CT have demonstrated the life-saving benefit of x-ray CT based screening for lung cancer in populations with much higher than normal risk of developing lung cancer, mostly due to an extensive smoking history. The proposed imaging method promises to provide improved detection rate at much lower radiation exposure and could just be extended to populations with intermediate risk level for developing lung cancer. Just like in existing screening protocols, the method would be used for serial scanning of both lungs for small nodules that demonstrate growth over time or have arisen de novo.

For example, in some embodiments, high-energy electrons are directed to lung tissue, and a detector system is configured to detect physical quantities of the electrons traversing the lung tissue, such that a computer system can reconstruct a 3D image with high spatial resolution of areas of increased density, such as nodules, and/or areas with high Z materials. In some embodiments, only one frame can collect sufficient data to generate a high-resolution 3D image, when a scattering reconstruction algorithm is utilized independently or in combination with a most likely path reconstruction. In other embodiments, multiple frames can further improve on image quality, for example by enhancing resolution of nodules and blood vessels.

In some embodiments of electron CT applied to imaging of lung tissue, multiple frames may be taken, and the frames can be reconstructed to form a time-resolved 3D image of the living lung tissue. In some embodiments, frames are continuously acquired for a time interval longer than a respiratory cycle. Multiple 3D reconstructions corresponding to different times are reconstructed and sorted into respiratory phase bins using various respiratory signals. In other embodiments, the eCT scanner is triggered by the respiratory signal, and the image data within the same respiratory phase bin are used to reconstruct CT images corresponding to that breathing phase.

The lung eCT scanner provides a significant dose advantage over traditional methods of thoracic imaging. Electron beams can be configured to deliver a total dose of less than or approximately equal to 1000 electrons per square millimeter of lung tissue to be screened.

The systems and methods disclosed herein can be implemented in hardware, software, firmware, or a combination thereof. Software can include computer-readable instructions stored in memory (e.g., non-transitory, tangible memory, such as solid state memory (e.g., ROM, EEPROM, FLASH, RAM), optical memory (e.g., a CD, DVD, Blu-ray disc, etc.), magnetic memory (e.g., a hard disc drive), etc.), configured to implement the algorithms on a general purpose computer, special purpose processors, or combinations thereof. For example, one or more computing devices, such as a processor, may execute program instructions stored in computer readable memory to carry out processes disclosed herein. Hardware may include state machines, one or more general purpose computers, and/or one or more special purpose processors. In some embodiment, one or multiple processors can be available as hardware processor resources of the system, and in some implementations the processors can be at different locations (e.g., coupled via a network). While certain types of user interfaces and controls are described herein for illustrative purposes, other types of user interfaces and controls may be used.

The embodiments discussed herein are provided by way of example, and various modifications can be made to the embodiments described herein. Certain features that are described in this disclosure in the context of separate embodiments can also be implemented in combination in a single embodiment. Conversely, various features that are described in the context of a single embodiment can be implemented in multiple embodiments separately or in various suitable subcombinations. Also, features described in connection with one combination can be excised from that combination and can be combined with other features in various combinations and subcombinations. Various features can be added to the example embodiments disclosed herein.

Also, various features can be omitted from the example embodiments disclosed herein.

Similarly, while operations are depicted in the drawings or described in a particular order, the operations can be performed in a different order than shown or described. Other operations not depicted can be incorporated before, after, or simultaneously with the operations shown or described. In certain circumstances, parallel processing or multitasking can be used. Also, in some cases, the operations shown or discussed can be omitted or recombined to form various combinations and subcombinations.

The following is claimed:

1. An imaging system for generating images of an object, the system comprising:
   a source of high-energy electrons configured to emit electrons with an energy greater than or equal to 10 MeV;
   a nozzle that directs the electrons emitted by the source towards the object when the system is in operation;
   a detector system configured to detect at least a position of the electrons before and after the electrons interact with the object; and
   a processor configured to:
      calculate an estimated path corresponding to an actual path taken by an individual electron within the object based at least in part on a detected position of the individual electron;
      determine from the estimated path of the individual electron an interaction between each image element of a digitized image of the object and the individual electron; and
      reconstruct the digitized image of the object based at least in part on the determined interactions between each image element and the individual electrons.

2. The imaging system of claim 1, wherein the object comprises living tissue.

3. The imaging system of claim 1, wherein the detector system is configured to detect a trajectory of the electrons after the electrons interact with the object, and wherein the estimated path corresponding to the actual path taken by the electron within the object is based at least in part on the individual electron's detected trajectory.

4. The imaging system of claim 1, wherein the detector system is configured to detect a momentum of the electrons after the electrons interact with the object, and wherein the estimated path corresponding to the actual path taken by the electron within the object is based at least in part on the individual electron's detected momentum.

5. The imaging system of claim 1, the processor further configured to:
   form a matrix A for the digitized image, wherein a matrix element $a_{i,j}$ corresponds to an intersection length of a $i^{th}$ electron with a $j^{th}$ voxel of the digitized image.

6. The imaging system of claim 1, the processor further configured to:
   identify one or more electrons that are likely to have undergone a large-angle scattering event;
   calculate a most likely scattering location for the electrons that are likely to have undergone the large-angle scattering event;
   form a matrix C for the digitized image, wherein a matrix element $c_{i,j}$ corresponds to a likelihood that a $i^{th}$ electron underwent a large-angle scattering event in a $j^{th}$ voxel of the digitized image.

7. The imaging system of claim 1, wherein the source of high-energy electrons is configured to emit electrons with an energy between 20 MeV and 200 MeV.

8. The imaging system of claim 1, further comprising a controller configured to control an emission of electrons by the source of high-energy electrons.

9. The imaging system of claim 8, wherein the controller is configured to cause the source of high-energy electrons to emit electrons in a series of one or more electron beams, wherein the one or more electron beams are configured to deliver a dose of electrons between approximately 10 and 1000 electrons per square millimeter of the object to be imaged.

10. The imaging system of claim 1, wherein the images are two-dimensional and the image element is a pixel.

11. The imaging system of claim 1, wherein the images are three-dimensional and the image element is a voxel.

12. A method for generating images of an object, the method comprising:
    delivering high-energy electrons with an energy greater than 10 MeV in a series of one or more electron beams to the object, wherein the one or more electron beams are configured to deliver a dose of electrons less than or equal to 1000 electrons per square millimeter of the object;
    measuring, with one or more particle detectors, data for the plurality of electrons that pass through the object, the measured data including information about first and second tracks for individual electrons, the first and second tracks corresponding to the electron's trajectories before and after its passage through the object, respectively, the measured data further including information about an interaction quantity of an individual electron resulting from its passage through the object;
    for individual electrons, calculating an estimated path corresponding to an actual path taken by the electron within the object based at least in part on the first and second tracks, the estimated path providing an estimate of the actual path;
    determining from the estimated path of an individual electron an interaction between each image element of a digitized image of the object and the individual electron; and
    reconstructing the digitized image of the object based at least in part on the determined interactions between each image element and individual electrons.

13. The method of claim 12, wherein the images are two-dimensional and the image element is a pixel.

14. The method of claim 12, wherein the images are three-dimensional and the image element is a voxel.

15. A method for performing radiography or computed tomography, the method comprising:
    delivering an electron beam to an object, the electron beam comprising a plurality of high-energy electrons;
    measuring, with one or more particle detectors, data for the plurality of electrons that pass through the object, the measured data including information about first and second tracks for individual electrons, the first and second tracks corresponding to the electron's trajectories before and after its passage through the object, respectively, the measured data further including information about an interaction quantity of an individual electron resulting from its passage through the object;
    for each individual electron, calculating an estimated path corresponding to an actual path taken by the electron within the object based at least in part on the first and second tracks, the estimated path providing an estimate of the actual path;
    arranging the interaction quantities and the estimated paths of the electron such that the passages of the electrons through the object is represented as a system of linear equations $Ax=b$ where x is a discrete object vector representing an object parameter distribution such that each element of the vector x represents a value of the object parameter distribution at a voxel in the object, b is a vector that represents the interaction quantities of the electrons resulting from interactions along their respective paths in the object, and A is a matrix that operates on the vector x to yield the vector b, the matrix A having information about the estimated paths of the electrons in the object, an element of the matrix A corresponding to an estimated intersection length of a selected electron in a corresponding voxel, the estimated intersection length being calculated as a straight-line approximation of the estimated path of the selected electron in the corresponding voxel so as to account for non-linearity of the actual paths of the electrons in the object and allow the system of linear equations to have a plurality of solutions;
    forming a matrix C for the digitized image, wherein a matrix element $c_{i,j}$ corresponds to a likelihood that a $i^{th}$ electron underwent a large-angle scattering event in a $j^{th}$ voxel of the digitized image;
    determining solutions for the systems of linear equations;
    calculating the object parameter distribution based on the determined solutions; and
    generating an image of the object based at least in part on the calculated object parameter distribution.

16. The method of claim 15, wherein the object parameter corresponds to any combination of one or more of the following: the relative stopping power of each image element in the object, the scattering power of each image element in the object, the attenuation of electron beam intensity occurring in each image element in the object, and to the likelihood of a large-angle scattering event occurring in each image element in the object.

17. A system for generating images of living organ tissue, the system comprising:
    a source of high-energy electrons configured to emit electrons with an energy greater than 10 MeV;
    a controller configured to control the emission of electrons by the source of high-energy electrons and to cause the source of high-energy electrons to emit electrons in a series of electron beams;
    a nozzle that directs the electrons emitted by the source towards living organ tissue when the system is in operation;
    a detector system configured to detect at least a position of the electrons before and after the electrons interact with the organ tissue; and
    a processor configured to iteratively:
        calculate an estimated path corresponding to an actual path taken by an individual electron within the object based at least in part on the individual electron's detected position;
        determine from the estimated path of an individual electron an interaction between each image element of a digitized image of the imaging object and the individual electron; and
        reconstruct the digitized image of the imaging object based at least in part on the determined interactions between each image element and individual electrons.

18. The system of claim 17, wherein the processor is configured to iteratively reconstruct two-dimensional or three-dimensional images of the living organ tissue including moving images of living organs.

19. The system of claim 18, wherein the living organ tissue comprises human extremities and body including living internal organs of a heart and coronary arteries, kidney stones, gallbladder stones, a head and brain, panoramic dental features, a breast, or a lung, wherein the digitized images with or without a contrast agent depict areas of interest differently.

20. The system of claim 19, wherein the internal organ is the lung, wherein the digitized image depicts higher density areas indicative of nodules differently from normal lung tissue or air.

* * * * *